United States Patent [19]

Serimian et al.

[11] Patent Number: Plant 5,591

[45] Date of Patent: Dec. 10, 1985

[54] NECTARINE TREE, "RED LION"

[76] Inventors: Lionel M. Serimian, 11310 E. Manning Ave.; Donald M. Serimian, 2961 McCall Ave., both of Selma, Calif. 93662

[21] Appl. No.: 578,951

[22] Filed: Feb. 10, 1984

[51] Int. Cl.[4] ..... A01H 5/03

[52] U.S. Cl. ..... Plt./41

[58] Field of Search ..... Plt./41

*Primary Examiner*—Robert E. Bagwill

[57] ABSTRACT

A new variety of nectarine tree broadly characterized by its general resemblance to that of the Red Jim (U.S. Plant Pat. No. 4,518) variety, but which bears fruit having a shallow, inconspicuous suture which colors an intense red substantially simultaneously and evenly with adjacent skin portions.

2 Drawing Figures

BACKGROUND OF THE NEW VARIETY

The present invention relates to a new and distinct variety of nectarine tree which has been denominated varietally as the "Red Lion" and is broadly similar to the Red Jim Nectarine Tree (U.S. Plant Pat. No. 4,518) in its bearing of medium-sized clingstone fruit whose skin has a red blush on a yellow ground color but from which it differs in bearing leaves of a deeper green color and in its bearing of fruit which is of a more spherical shape and has an inconspicuous, shallow suture which colors evenly and substantially simultaneously with the skin adjacent thereto, and whose skin is characterized by a high intensity of coloration and sheen.

ORIGIN AND ASEXUAL REPRODUCTION OF THE NEW VARIETY

The nectarine tree of the present invention was discovered by both of us in 1979 growing as a hybrid resulting from the pollination of a Red Free Nectarine Tree (believed unpatented) by pollen from a Regal Grand Nectarine Tree (U.S. Plant Pat. No. 1,751) in an orchard of Red Free Nectarine Trees owned by us and located at the corner of Dinuba Avenue and Newmark Avenue, near Selma, Country of Fresno, State of California.

We asexually reproduced the hybrid by grafting onto trees in an orchard owned by us at the northeast corner of Dinuba Avenue and Del Rey Avenue in Selma, in the County of Fresno, in the State of California. The fruit and tree characteristics resulting from this grafting have proved identical to those of the original hybrid.

SUMMARY OF THE NEW VARIETY

The instant variety of nectarine tree is characterized by its general resemblance to the Red Jim Nectarine Tree (U.S. Plant Pat. No. 4,518) in its bearing of medium-sized, clingstone, red-skinned fruit maturing approximately with that of the Red Jim. However, the fruit of the instant variety is distinguished from that of the Red Jim by its more spherical configuration, by its suture which is shallow and virtually inconspicuous, coloring an intense red substantially evenly and simultaneously with the skin adjacent thereto, and by the high degree of sheen exhibited by its skin. The new variety further is distinguished as to novelty by its dark green leaves.

The new nectarine tree bears fruit whose skin attains an intense red coloration ranging from Horse Chestnut (Plate 8-J-5) to Red Cross (Plate 4-L-6) and Afghan Red (Plate 5-L-6) on a ground color of Primrose Yellow (Plate 10-J-4). The fruit matures between August 10 and August 20.

BRIEF DESCRIPTION OF THE DRAWING

The accompanying drawing is a color photograph of three mature nectarines of the subject variety with one of the fruits divided along the suture plane to show the flesh color and stone characteristics, together with a representative twig bearing characteristic leaves.

DETAILED DESCRIPTION

Referring more specifically to the pomological details of the new and distinct variety of nectarine tree, the following has been observed under the ecological conditions prevailing in the designated orchard in Fresno County, Calif. All color code plate identifications are by reference to A. Maerz and M. Paul, *Dictionary of Color,* Second Edition, 1950.

TREE

Size: Undetermined.
Vigor: Vigorous.
Productivity: Productive.
Regularity of bearing: Regular.
Trunk:
- *Diameter in relation to length.*—Medium.
- *Color of new wood.*—Green to brown.

Leaves:
- *Size.*—Medium.
- *Length.*—160 mm. average.
- *Width.*—30 to 53 mm.; average 45 mm.
- *Shape.*—Lanceolate, apex acuminate.
- *Color.*—Upper side — Plate 23-H-7; Under side — Linkin Green, Plate 23-J-4.
- *Marginal form.*—Serrulate.
- *Petiole.*—Length — 8 to 10 mm.; thickness — 2 mm.
- *Stem glands.*—Number — 2 to 5, usually 2 to 3; 2 opposite on petiole at base of leaf with others on leaf.
- *Size.*—1 to 1½ mm. in length.
- *Type.*—Reniform.
- *Stipules.*—Older leaves exstipulate, newer leaves small, 8 to 15 mm. long and narrow, less than ½ mm.; red or green.

Flower Buds:
*Size.*—Medium, 5 to 7 mm. in diameter.
*Shape.*—Oval.
*Surface.*—Medium, pink to reddish-pink.
Flowers:
*Date of first bloom.*—Feb. 25, 1983.
*Size.*—5 cm. average in diameter.
*Pedicel.*—Normal.
*Petals.*—Light pink, 2 to 2.5 cm. in length.
*Nectaries.*—Normal.
*Stamens.*—14 mm. in length (average).
*Pistil.*—Generally longer than stamens, 1.5 to 2.0 cm. long.

FRUIT

Maturity: August 10 to August 20.
Size:
*Uniformity.*—Generally uniform.
*Axial diameter.*—70 mm. average.
*Diameter transverse in suture plane.*—67 to 78 mm., average 73 mm.
*Diameter transverse at right angles to suture plane.*—64 to 75 mm., average 73 mm.
Form:
*Symmetry.*—Generally globose, asymmetric.
*Uniformity.*—Uniform.
*Suture.*—Shallow, inconspicuous, lips unequal; extends completely from apex to stem cavity on ventral side.
*Ventral surface.*—Lips unequal.
*Stem cavity.*—Length — 25 mm.; width — 17 mm.; depth — 15 mm.
*Base.*—Shoulders rounded.
*Apex.*—Rounded.
*Pistil point.*—Slight to absent.
*Stem.*—Normal.
Skin:
*Texture.*—Smooth.
*Color.*—Brilliant Red with high sheen, ranging from Horse Chestnut (Plate 8-J-5) to Red Cross (Plate 4-L-6) to Afghan Red (Plate 5-L-6) on a ground color of Primrose Yellow (Plate 10-J-4); mottled or streaked, particularly at base, giving fruit an appearance similar to an apple. Suture colors evenly with surrounding skin.
*Pubescence.*—None.
Flesh:

*Color.*—Goldenrod (Plate 10-L-5) with Red Cross (Plate 4-L-6) to Afghan Red (Plate 5-L-6) color bleed extending from pit cavity into flesh.
*Flavor.*—Low acid, not tart.
*Texture.*—Firm.
*Fibers.*—None apparent.
*Ripening.*—Even.
*Eating quality.*—Good.
Stone: Cling, tenacious to flesh.
*Fibers.*—Few, short fibers at stone.
*Size.*—Length — 34 mm.; width — 26 mm.; thickness — 18 mm.
*Form.*—Oval, slightly pointed at apex.
*Dorsal edge.*—Groove shallow or lacking, no wing.
*Ventral edge.*—Grooves shallow, $\frac{2}{3}$ to $\frac{3}{4}$ of the distance from the base to the apex, wing small or lacking.
*Splitting tendency.*—None observed.
Use: Fresh market.
Keeping quality: Excellent.
Shipping quality: Excellent.
Resistance to disease: Normal.
Varietal name: "Red Lion".

Although the new variety of nectarine tree possesses the described characteristics under the growing conditions prevailing in Fresno County, Calif., in the central portion of the San Joaquin Valley, it is to be understood that variations of the usual magnitude in characteristics incident to changes in growing conditions, fertilization, pruning and pest control are to be expected.

Having thus described our new variety of nectarine tree, what we claim as new and desire to secure by Plant Letters Patent is:

1. A new and distinct variety of nectarine tree substantially as illustrated and described, bearing fruit which mature approximately with that of the Red Jim (U.S. Plant Pat. No. 4,518) which it most nearly resembles, in its regular and productive bearing of medium-sized, clingstone fruit, but from which it is distinguished as to novelty by its fruit having a more spherical shape with a shallow, virtually inconspicuous suture coloring substantially simultaneously and evenly with the skin of the fruit as the fruit matures and by its leaves whose upper surfaces have a more vivid and darker green color.

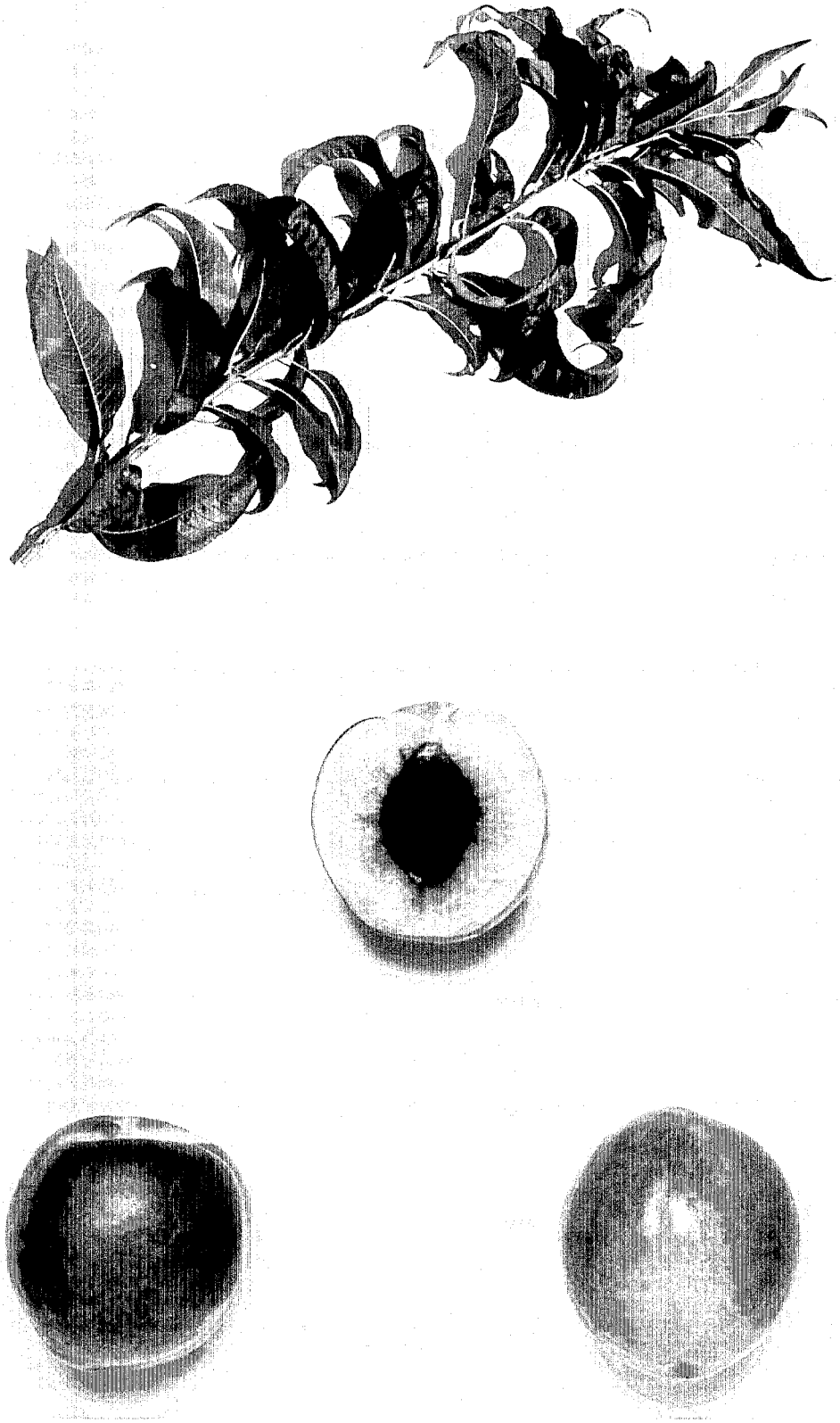

* * * * *